(12) United States Patent
Kamei et al.

(10) Patent No.: US 9,518,041 B2
(45) Date of Patent: Dec. 13, 2016

(54) (+)-5-(3,4-DIFLUOROPHENYL)-5-[(3-METHYL-2-OXOPYRIDIN-1(2H)-YL) METHYL]IMIDAZOLIDINE-2,4-DIONE AND DRUG CONTAINING SAME

(71) Applicant: KAKEN PHARMACEUTICAL CO., LTD., Bunkyo-ku, Tokyo (JP)

(72) Inventors: Noriyuki Kamei, Kyoto (JP); Daigo Kamimura, Kyoto (JP); Yoshitake Sumikawa, Kyoto (JP); Shota Tokuoka, Kyoto (JP)

(73) Assignee: KAKEN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/895,768

(22) PCT Filed: Jun. 6, 2014

(86) PCT No.: PCT/JP2014/065060
§ 371 (c)(1),
(2) Date: Dec. 3, 2015

(87) PCT Pub. No.: WO2014/196623
PCT Pub. Date: Nov. 12, 2014

(65) Prior Publication Data
US 2016/0130248 A1    May 12, 2016

(30) Foreign Application Priority Data
Jun. 7, 2013    (JP) .................. 2013-120692

(51) Int. Cl.
*A01N 43/40*    (2006.01)
*C07D 401/06*    (2006.01)
*A61K 47/10*    (2006.01)
*A61K 9/06*    (2006.01)
*A61K 9/00*    (2006.01)
*A61K 9/10*    (2006.01)
*A61K 9/20*    (2006.01)

(52) U.S. Cl.
CPC .......... *C07D 401/06* (2013.01); *A61K 9/0014* (2013.01); *A61K 9/06* (2013.01); *A61K 9/10* (2013.01); *A61K 9/2054* (2013.01); *A61K 47/10* (2013.01)

(58) Field of Classification Search
CPC .................................. C07D 401/06

USPC ..................................................... 514/341
See application file for complete search history.

(56) References Cited

U.S. PATENT DOCUMENTS

| | | |
|---|---|---|
| 2004/0242928 A1 | 12/2004 | Shimano et al. |
| 2006/0205797 A1 | 9/2006 | Yu et al. |
| 2006/0276506 A1 | 12/2006 | Yu et al. |
| 2007/0197564 A1 | 8/2007 | Lavey et al. |
| 2007/0219218 A1 | 9/2007 | Yu et al. |
| 2007/0265299 A1 | 11/2007 | Lavey et al. |
| 2015/0166506 A1* | 6/2015 | Kamei ............. C07D 401/14 546/256 |

FOREIGN PATENT DOCUMENTS

| | | |
|---|---|---|
| WO | 03022801 A1 | 3/2003 |
| WO | 2004024721 A1 | 3/2004 |
| WO | 2004033632 A2 | 4/2004 |
| WO | 2004108086 A2 | 12/2004 |
| WO | 2005085232 A1 | 9/2005 |
| WO | 2006019768 A1 | 2/2006 |
| WO | 2007084415 A2 | 7/2007 |
| WO | 2007084451 A1 | 7/2007 |
| WO | 2007084455 A1 | 7/2007 |
| WO | 2010036640 A2 | 4/2010 |
| WO | 2010054278 A2 | 5/2010 |
| WO | 2013085016 A1 | 6/2013 |
| WO | 2013085017 A1 | 6/2013 |

OTHER PUBLICATIONS

Nelson, F.C. et al., Exp. Opin. Invest. Drugs; The therapeutic potential of small molecule TACE inhibitors; 1999, 8, 383-392.
Murumkar, P.R. et al., Exp. Opin. Ther. Patents; Novel TACE inhibitors in drug discovery: a review of patented compounds; 2010, 20, 31-57.
DasGupta, S. et al. Bioorg. Med. Chem; Current perspective of TACE inhibitors: A review; 2009, 17, 444-459.
Yu, W et al., Bioorg. Med. Chem. Lett.; Biaryl substituted hydantoin compounds as TACE inhibitors; 2010, 20, 5286-5289.
Yu, W. et al., Bioorg. Med. Chem. Lett.; Discovery and SAR of hydantoin TACE inhibitors; 2010, 20, 1877-1880.

* cited by examiner

*Primary Examiner* — Nizal Chandrakumar
(74) *Attorney, Agent, or Firm* — Sughrue Mion, PLLC

(57) ABSTRACT

Provided is (+)-5-(3,4-difluorophenyl)-5-[(3-methyl-2-oxopyridin-1(2H)-yl)methyl]imidazolidine-2,4-dione or a salt thereof. Also provided is a drug containing as the active ingredient (+)-5-(3,4-difluorophenyl)-5-[(3-methyl-2-oxopyridin-1(2H)-yl)methyl]imidazolidine-2,4-dione or a salt thereof.

21 Claims, No Drawings

(+)-5-(3,4-DIFLUOROPHENYL)-5-[(3-METHYL-2-OXOPYRIDIN-1(2H)-YL) METHYL]IMIDAZOLIDINE-2,4-DIONE AND DRUG CONTAINING SAME

CROSS REFERENCE TO RELATED APPLICATIONS

This application is a National Stage of International Application No. PCT/JP2014/065060 filed Jun. 6, 2014, claiming priority based on Japanese Patent Application No. 2013-120692 filed Jun. 7, 2013, the contents of all of which are incorporated herein by reference in their entirety.

TECHNICAL FIELD

The present invention relates to optically pure (+)-5-(3, 4-difluorophenyl)-5-[(3-methyl-2-oxopyridin-1(2H)-yl) methyl]imidazolidine-2,4-dione, or a salt thereof, and a pharmaceutical containing thereof, as an active ingredient, which have a tumor necrosis factor-alpha (TNF-α) converting enzyme (TACE) inhibitory effect.

BACKGROUND ART

TNF-α is one of the cytokines secreted from macrophages, monocytes and the like activated by exogenous and endogenous factors. TNF-α is extensively involved in promoting the secretion of various cytokines and in protecting against infection. However, the persistent and excessive production and secretion of TNF-α cause overproduction of inflammatory cytokines, apoptosis of cells, and interference of intracellular signal transduction and the like, resulting in the primary and secondary tissue damage, and eventually becomes a factor responsible for etiology and exacerbation of various disorders (see Non-Patent Literature 1). Therefore, to treat a pathological condition thought to be caused by the excessive production and secretion of TNF-α, it is important to suppress the production and secretion of TNF-α, or to suppress the action of TNF-α. Examples of such diseases in which TNF-α participate include rheumatoid arthritis, systemic lupus erythematosus (SLE), Crohn's disease, Behcet's disease, multiple sclerosis, arteriosclerosis, myasthenia gravis, diabetes, sepsis, acute infectious diseases, asthma, atopic dermatitis, contact dermatitis, psoriasis, acne, fever, anemia and the like.

Tumor necrosis factor alpha converting enzyme (TACE) (also called ADAM 17), which is classified in the ADAM (a disintegrin and metalloproteinase) family, is a membrane-bound protease having zinc at a catalytic site thereof and TACE produces soluble TNF-α by cleaving membrane-bound TNF-α (pro-TNF-α). Therefore, compounds that inhibit the enzyme action of TACE are likely to suppress the production of soluble TNF-α, thereby serving as a therapeutic agent for the above-described various disease conditions caused by TNF-α. Based on this, research into compounds having a TACE inhibitory effect is being actively carried out (see Non-Patent Literature 2 and 3).

On the other hand, matrix metalloproteinase (also called matrixin) (MMP) is a protease having zinc at a catalytic site thereof and has an effect of degrading the extracellular matrix. Approximately 20 subtypes of MMP are known.

A compound that inhibits certain types of MMP has been reported as inhibiting the production of TNF-α as well (see Non-Patent Literature 4). Further, since TACE and MMP are both enzymes having zinc at a catalytic site and also have a similar three-dimensional structure, compounds that inhibit both MMP and TACE have also been reported (see Non-Patent Literature 5). However, it has been reported that rats continuously administered with an agent which inhibits many kinds of MMPs at the same time had a hypertrophic degeneration on the cartilage growth plates (see Non-Patent Literature 6), and that MT1-MMP (MMP-14) knockout mice were observed to present a symptom of arthritis (see Non-Patent Literature 7). There are concerns about the various side-effects that occur due to MMP inhibition based on these reports. In addition, since most of MMPs are involved in the maintenance and homeostasis of the extracellular matrix, which form the basic structure of a living body, inhibiting the catalytic activities of many MMPs nonselectively is likely to cause serious adverse effects on the living body. Therefore, it is preferred that a compound directed to TNF-α production inhibition based on TACE inhibition does not essentially exhibit an inhibitory effect against MMPs.

Patent Literature 1, Non-Patent Literature 8 and Non-Patent Literature 9 contain reports about compounds that selectively inhibit TACE. Further, Patent Literature 2 to Patent Literature 10 contain reports about TACE inhibitor compounds that have a hydantoin structure.

CITATION LIST

Patent Literature

[Patent Literature 1] WO 03/022801 Pamphlet
[Patent Literature 2] WO 10/054278 Pamphlet
[Patent Literature 3] WO 10/036640 Pamphlet
[Patent Literature 4] WO 07/084455 Pamphlet
[Patent Literature 5] WO 07/084415 Pamphlet
[Patent Literature 6] WO 06/019768 Pamphlet
[Patent Literature 7] WO 05/085232 Pamphlet
[Patent Literature 8] WO 04/024721 Pamphlet
[Patent Literature 9] WO 04/033632 Pamphlet
[Patent Literature 10] WO 04/108086 Pamphlet

Non Patent Literature

[Non-Patent Literature 1] Aggarwall B. B., Puri R. K., eds. 1995. Human Cytokines: Their Role in Disease and Therapy. Cambridge, Mass., USA: Blackwell Sci.
[Non-Patent Literature 2] Nelson, F. C. et al., Exp. Opin. Invest. Drugs 1999, 8, 383-392
[Non-Patent Literature 3] Murumkar, P. R. et al., Exp. Opin. Ther. Patents 2010, 20, 31-57
[Non-Patent Literature 4] Mohler, K. M. et al., Nature 1994, 370, 218-220
[Non-Patent Literature 5] DasGupta, S. et al., Bioorg. Med. Chem., 2009, 17, 444-459
[Non-Patent Literature 6] Nakajima, M., The Bone 2001, 15, 161-166
[Non-Patent Literature 7] Holmbeck, K. et al., Cell 1999, 99, 81-92
[Non-Patent Literature 8] Yu, W. et al., Bioorg. Med. Chem. Lett., 2010, 20, 1877-1880
[Non-Patent Literature 9] Yu, W. et al., Bioorg. Med. Chem. Lett., 2010, 20, 5286-5289

SUMMARY OF INVENTION

Technical Problem

In view of such circumstances, there is a continuing need for a TNF-α production inhibitor that is based on TACE inhibition. And, the discovery of a novel compound exhibiting a TACE inhibitory effect is desired. As described above, from the point of safety, it is considered that a novel compound directed to TNF-α production inhibition based on TACE inhibition needs to exhibit hardly any inhibitory effects against MMP, namely, that the compound needs to have selectivity against MMP. On the other hand, from the point of the usefulness of such compound, it may be more desirable that the compound has another useful property.

The present invention has been accomplished with the aim on the treatment and prevention of such TNF-α-related diseases. Namely, the present invention is directed to providing a novel compound, or a salt thereof, that exhibits a selective TACE inhibitory effect (i.e. a weak inhibitory effect against MMP), and to providing a pharmaceutical having such compound as an active ingredient.

As a result of diligent research into the above problems, the present inventors made the surprising discovery that (+)-5-(3,4-difluorophenyl)-5-[(3-methyl-2-oxopyridin-1 (2H)-yl)methyl]imidazolidine-2,4-dione has an excellent selective TACE inhibitory activity, and favorable solubility in a base. The present inventors progressed with their research to complete the present invention on the basis of this finding.

Specifically, the present invention relates to at least the following respective aspects.

(1) (+)-5-(3,4-Difluorophenyl)-5-[(3-methyl-2-oxopyridin-1 (2H)-yl)methyl]imidazolidine-2,4-dione or a salt thereof.
(2) A pharmaceutical containing as an active ingredient the compound according to (1) or a salt thereof.
(3) The pharmaceutical according to (2), substantially not containing (−)-isomer.
(4) The pharmaceutical according to (2) or (3), wherein 95 weight % or more of the total amount of the 5-(3,4-difluorophenyl)-5-[(3-methyl-2-oxopyridin-1(2H)-yl) methyl]imidazolidine-2,4-dione or a salt thereof in the pharmaceutical is (+)-isomer.
(5) The pharmaceutical according to (4), wherein 98 weight % or more of the total amount of the 5-(3,4-difluorophenyl)-5-[(3-methyl-2-oxopyridin-1(2H)-yl)methyl]imidazolidine-2,4-dione or a salt thereof in the pharmaceutical is (+)-isomer.
(6) The pharmaceutical according to (5), wherein 99.5 weight % or more of the total amount of the 5-(3,4-difluorophenyl)-5-[(3-methyl-2-oxopyridin-1(2H)-yl) methyl]imidazolidine-2,4-dione or a salt thereof in the pharmaceutical is (+)-isomer.
(7) The pharmaceutical according to any one of (2) to (6), wherein the pharmaceutical is an external preparation.
(8) The pharmaceutical according to (7), wherein the external preparation is selected from the group consisting of a lotion, cream, liquid and ointment.
(9) The pharmaceutical according to (7) or (8), containing pharmaceutically acceptable glycols.
(10) The pharmaceutical according to (9), wherein the pharmaceutically acceptable glycols is propylene glycol or butylene glycol.
(11) The pharmaceutical according to any one of (7) to (10), containing water in the formulation.
(12) The pharmaceutical according to any one of (7) to (11), containing as an active ingredient 1 w/w % or more (+)-5-(3,4-difluorophenyl)-5-[(3-methyl-2-oxopyridin-1 (2H)-yl)methyl]imidazolidine-2,4-dione or a salt thereof.
(13) The pharmaceutical according to (12), containing as an active ingredient 3 w/w % or more (+)-5-(3,4-difluorophenyl)-5-[(3-methyl-2-oxopyridin-1(2H)-yl)methyl]imidazolidine-2,4-dione or a salt thereof.
(14) The pharmaceutical according to any one of (2) to (13), being transdermally administered.
(15) The pharmaceutical according to any one of (2) to (14), wherein the pharmaceutical is a preventive or treatment agent for a skin disease.
(16) The pharmaceutical according to (15), wherein the skin disease is one or more selected from the group consisting of a localized scleroderma, atopic dermatitis, contact dermatitis, psoriasis, and acne.
(17) A method of producing (+)-5-(3,4-difluorophenyl)-5-[(3-methyl-2-oxopyridin-1(2H)-yl)methyl]imidazolidine-2,4-dione, comprising optically resolving a racemate (±)-5-(3,4-difluorophenyl)-5-[(3-methyl-2-oxopyridin-1 (2H)-yl)methyl]imidazolidine-2,4-dione by chromatography using a column for optical separation.
(18) (+)-5-(3,4-Difluorophenyl)-5-[(3-methyl-2-oxopyridin-1(2H)-yl)methyl]imidazolidine-2,4-dione obtainable by optically resolving a racemate (±)-5-(3,4-difluorophenyl)-5-[(3-methyl-2-oxopyridin-1(2H)-yl)methyl]imidazolidine-2,4-dione by chromatography using a column for optical separation.
(19) A mixture of (+)- and (−)-isomers of 5-(3,4-difluorophenyl)-5-[(3-methyl-2-oxopyridin-1(2H)-yl)methyl]imidazolidine-2,4-dione, wherein the (+)-isomer exists at 90% ee or more to the (−)-isomer.
(20) The mixture according to (19), wherein the (+)-isomer exists at 96% ee or more to the (−)-isomer.
(21) The mixture according to (19) or (20), wherein the (+)-isomer exists at 99% ee or more to the (−)-isomer.

Advantageous Effects of the Invention

The (+)-5-(3,4-difluorophenyl)-5-[(3-methyl-2-oxopyridin-1(2H)-yl)methyl]imidazolidine-2,4-dione or a salt thereof, according to the present invention has an excellent selective TACE inhibitory effect, and is effective as a preventive or therapeutic agent for a TNF-α-related disease.

DESCRIPTION OF EMBODIMENTS

Next, the present invention is described in more detail.

First, the salt of (+)-5-(3,4-difluorophenyl)-5-[(3-methyl-2-oxopyridin-1(2H)-yl)methyl]imidazolidine-2,4-dione according to the present invention is not specifically limited as long as it is a pharmacologically acceptable salt. Such salts include, for example, a salt with an inorganic base, a salt with an organic base and the like. Examples of a salt with an inorganic base include an alkali metal salt and an alkaline earth metal salt, such as a lithium salt, a sodium salt, a potassium salt, a magnesium salt, a calcium salt, and a barium salt. Examples of a salt with an organic base include a triethylamine salt, a pyridine salt, an ethanolamine salt, a cyclohexylamine salt, a dicyclohexylamine salt, a dibenzylethanolamine salt, a benzylamine salt, a 2-methylbenzylamine salt, an α-methylbenzylamine salt, a brucine salt, a quinine salt, a quinidine salt, a cinchonine salt, a cinchonidine salt, an arginine salt and the like.

Next, the method for producing (+)-5-(3,4-difluorophenyl)-5-[(3-methyl-2-oxopyridin-1(2H)-yl)methyl]imidazolidine-2,4-dione according to the present invention (may be referred to hereinafter as "(+)-(I)") according to the present invention is described. This compound can be produced by various methods. For example, the compound can be efficiently produced based on the production method shown below.

Specific examples of the "protecting group" used in the following production method include, as that of a hydroxyl group or a carboxyl group, a tert-butyl group, a benzyl group, an o-methylbenzyl group, a p-nitrobenzyl group, a p-methoxybenzyl group, an o-chlorobenzyl group, a 2,4-dichlorobenzyl group, a p-bromobenzyl group, an allyl group, a tert-butoxycarbonyl group, a benzyloxycarbonyl group, an o-methylbenzyloxycarbonyl group, a p-nitrobenzyloxycarbonyl group, a p-methoxybenzyloxycarbonyl group, an o-chlorobenzyloxycarbonyl group, a 2,4-dichlorobenzyloxycarbonyl group, a p-bromobenzyloxycarbonyl group, an allyloxycarbonyl group, a methoxymethyl group, a tetrahydropyranyl group and the like. As that of a carbonyl protecting group, examples include a protecting group derived from ethanediol, propanediol, mercaptoethanol, mercaptopropanol, ethanedithiol, propanedithiol and the like.

Production Method-1 (Production Method Using a Chiral Column)

The compound (+)-(I) can be produced, for example, based on the method shown in the following scheme 1 (step 1 to step 3).

Scheme 1

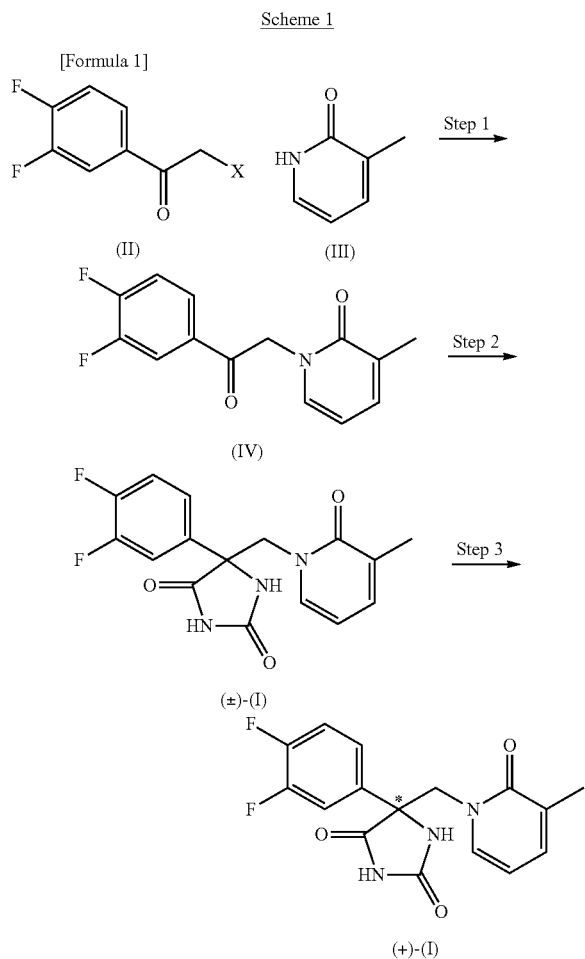

(wherein X represents a chlorine atom, a bromine atom or an iodine atom. The asterisk (*) denotes being an optically pure form.)

<Step 1>

In step 1, a compound represented by the general formula (II) and the compound (III) are reacted in the presence of a base to produce the compound (IV). Instead of the compound (III), a compound (V),

which is a tautomer of the compound (III), may be used. Examples of preferred bases include potassium carbonate, sodium carbonate, cesium carbonate, sodium hydride and the like. In addition, to promote this reaction, an additive may be added. Examples of such additives include potassium iodide, sodium iodide, tetrabutylammonium iodide, potassium bromide, sodium bromide, tetrabutylammonium bromide and the like. The reaction solvent is not specifically limited as long as it does not significantly inhibit the reaction. Examples of preferred reaction solvents include, for example, N,N-dimethylformamide, dimethyl sulfoxide, acetone, acetonitrile, methanol, ethanol, tetrahydrofuran, 1,4-dioxane, 2-methoxyethanol, a mixed solvent thereof and the like. Further, water can be added to the reaction solvent. In a case where water is added, although the added amount of water is not especially limited, it is preferably 10% or less to the reaction solvent, for example. Although the reaction temperature is not especially limited, for example, from room temperature to 60° C. is preferred. The reaction time is preferably from 1 hour to 2 days.

<Step 2>

In step 2, compound (±)-(I), the racemate, is produced by reacting compound (IV) with a cyanide in the presence of a salt. Examples of preferred salts include ammonium carbonate, ammonium bicarbonate and the like. Examples of preferred cyanides include potassium cyanide, sodium cyanide and the like. The reaction solvent is not specifically limited as long as it does not significantly inhibit the reaction. Examples of preferred reaction solvents include, for example, water, ammonia water, methanol, ethanol, tetrahydrofuran, 1,4-dioxane, N,N-dimethylformamide, a mixed solvent thereof and the like. The reaction temperature is not specifically limited. For example, 50° C. to 120° C. is preferred. The reaction time is preferably from 1 hour to 10 days. The compound (±)-(I) that is obtained in this step can also be obtained in the form of its salt depending on the work-up procedure of this reaction.

<Step 3>

In step 3, the compound (±)-(I) is optically resolved using a chiral column to produce compound (+)-(I). Optically resolution using a chiral column can be conducted in accordance with a method known to a skilled person in the art; see, for example, "Separation of Optical Isomers" (Kikan Kagaku Sosetsu, No. 6, 1989, Edited by The Chemical Society of Japan, Scientific Societies Press). Various chiral columns to be used are commercially available and appropriate one can be selected. CHIRALPAK AD (manufactured by Daicel Corporation) is preferable in terms of favorable resolution ability of both optical isomers.

The above identified compound (IV) can also be produced in Scheme 2 below (Step 4 to Step 8).

Scheme 2

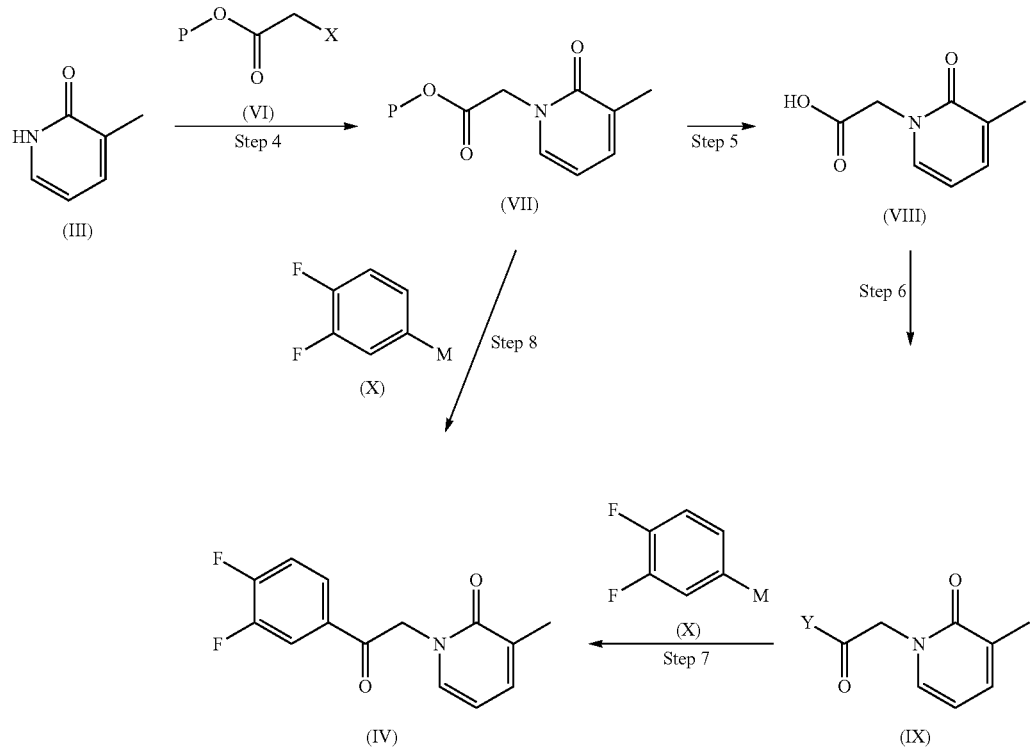

(wherein X represents a chlorine atom, a bromine atom or an iodine atom; Y represents an amine-derived group as shown below;

[Formula 4]

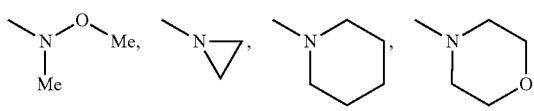

P represents a protection group; M represents MgBr, MgCl, Li, ZnBr or ZnCl.)

<Step 4>

In step 4, the compound (III) and a compound represented by the general formula (VI) are reacted in the presence of a base to produce a compound represented by the general formula (VII). Instead of the compound (III), a compound (V),

[Formula 5]

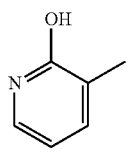

which is a tautomer of the compound represented by formula (III), may be used. Examples of preferred bases include potassium carbonate, sodium carbonate, cesium carbonate, sodium hydride and the like. In addition, to promote this reaction, an additive may be added. Examples of such additives include potassium iodide, sodium iodide, tetrabutylammonium iodide, potassium bromide, sodium bromide, tetrabutylammonium bromide and the like. The reaction solvent is not specifically limited as long as it does not significantly inhibit the reaction. Examples of preferred reaction solvents include, for example, N,N-dimethylformamide, dimethyl sulfoxide, acetone, acetonitrile, methanol, ethanol, tetrahydrofuran, 1,4-dioxane, 2-methoxyethanol, a mixed solvent thereof and the like. Although the reaction temperature is not specifically limited, for example, from room temperature to 60° C. is preferred. The reaction time is preferably from 1 hour to 2 days.

<Step 5>

In step 5, the compound represented by the general formula (VII) is hydrolyzed in an aqueous inorganic base to produce compound (VIII). Examples of preferred aqueous inorganic bases include aqueous sodium hydroxide, aqueous potassium hydroxide, aqueous lithium hydroxide and the like. The reaction solvent is not specifically limited as long as it does not significantly inhibit the reaction. Examples of preferred reaction solvents include, for example, water, methanol, ethanol, tetrahydrofuran, 1,4-dioxane, a mixed solvent thereof and the like. Although the reaction temperature is not specifically limited, for example, from room temperature to 60° C. is preferred. The reaction time is preferably from 1 to 96 hours. The compound (VIII) is obtained in a form of a carboxylic acid, a sodium carboxylate, a potassium carboxylate, a lithium carboxylate, a mixture of a carboxylic acid with an inorganic salt (sodium chloride, lithium chloride or potassium chloride) or the like.

<Step 6>

In step 6, the compound (VIII) obtained in step 5 is converted to an activated carboxylic acid derivative, and then reacted with an amine or a salt thereof to produce a compound (IX). Examples of the activated carboxylic acid derivative include an acid halide obtained by treating the compound (VIII) with thionyl chloride, phosphorus oxychloride, phosphorus pentachloride, oxalyl chloride, thionyl bromide or the like; an active ester obtained by condensation reaction of the compound (VIII) with a condensing agent such as 1-ethyl-3'-(3'-dimethylaminopropyl)carbodiimide hydrochloride or dicyclohexylcarbodiimide; and a mixed anhydride obtained by reacting the compound (VIII) with ethyl chloroformate, pivaloyl chloride, isobutyl chloroformate or the like. Further, in this reaction, a base may be added as necessary. Examples of such base include an organic amine, such as triethylamine, tert-butylamine, pyridine, and N-methylmorpholine. Triethylamine, pyridine, or N-methylmorpholine is preferred. The reaction solvent is not specifically limited as long as it does not significantly inhibit the reaction. Examples of preferred reaction solvents include, for example, N,N-dimethylformamide, tetrahydrofuran, dichloromethane, chloroform and the like. Although the reaction temperature is not specifically limited, for example, from 0° C. to 60° C. is preferred. The reaction time is preferably from 1 to 96 hours.

<Step 7>

In step 7, compound (IV) is produced by reacting the compound (IX) obtained in Step 6 and a compound represented by the general formula (X). As the compound (X), recited are, by the use of a compound represented by the general formula (XI)

[Formula 6]

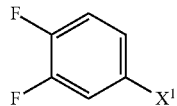

(XI)

(wherein $X^1$ represents a chlorine atom, a bromine atom or an iodine atom) as a material, a lithium reagent prepared by halogen-metal exchange reaction using a base such as n-butyllithium, sec-butyllithium, tert-butyllithium; a Grignard reagent prepared by the use of magnesium, isopropylmagnesium bromide, isopropylmagnesium chloride or the like; a zinc reagent prepared by the use of activated zinc, zinc bromide, zinc chloride or the like. The reaction solvent is not specifically limited as long as it does not significantly inhibit the reaction. Examples of preferred reaction solvents include, for example, tetrahydrofuran, diethyl ether, 1,4-dioxane or dimethoxyethane. Although the reaction temperature is not specifically limited, for example, from −100° C. to room temperature is preferred. The reaction time is preferably from 1 to 24 hours.

<Step 8>

In step 8, in a similar manner to Step 7, compound (IV) is produced by reacting a compound represented by the general formula (VII) with a compound represented by the general formula (X).

In addition, the above mentioned compound (II) can be produced, as recited below, by a method as described in Scheme 3 (Step 9 to Step 11).

Scheme 3

[Formula 7]

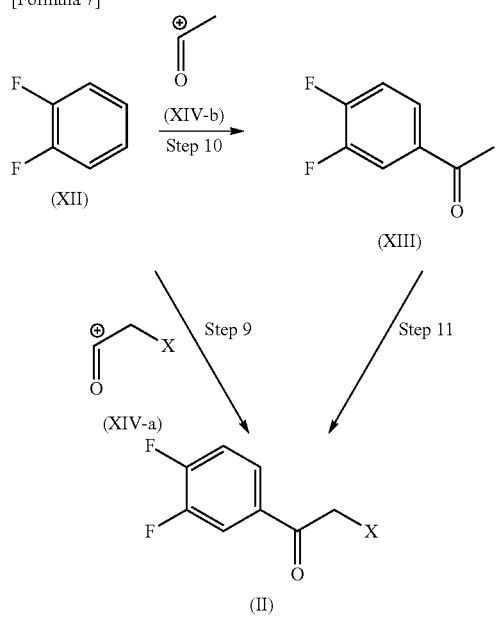

(wherein X represents a chlorine atom, a bromine atom or an iodine atom).

<Step 9>

In step 9, compound (II) is produced by reacting compound (XII) with an intermediate represented by the general formula (XIV-a). Examples of the intermediate (XIV-a) include an active intermediate obtained from an acid halide and a Lewis acid; an active intermediate obtained from an acid anhydride and a Lewis acid; and an active intermediate obtained from a carboxylic acid and a dehydrating agent. Examples of the acid halide include chloroacetyl chloride, chloroacetyl bromide, bromoacetyl bromide, bromoacetyl chloride, iodoacetyl chloride and the like. Examples of the acid anhydride include chloroacetic anhydride, bromoacetic anhydride, iodoacetic anhydride and the like. Examples of the carboxylic acid include chloroacetic acid, bromoacetic acid, iodoacetic acid and the like. Examples of the Lewis acid include aluminum chloride, zinc chloride and the like. Examples of the dehydrating agent include phosphorus pentoxide and the like. The reaction solvent is not specifically limited as long as it does not significantly inhibit the reaction. Examples of preferred reaction solvents include, for example, dichloromethane, dichloroethane and the like. Further, the reaction solvent may not be used. Although the reaction temperature is not specifically limited, for example, from 0° C. to 100° C. is preferred. The reaction time is preferably from 1 to 24 hours.

<Step 10>

In step 10, compound (XIII) is produced by reacting compound (XII) with an intermediate represented by the general formula (XIV-b). Examples of the intermediate (XIV-b) include an active intermediate obtained from an acetyl halide and a Lewis acid; an active intermediate obtained from an acetic anhydride and a Lewis acid; and an active intermediate obtained from acetic acid and a dehydrating agent. Examples of the acetyl halide include acetyl chloride, acetyl bromide, acetyl iodide. Examples of the Lewis acid include aluminum chloride, zinc chloride and the like. Examples of the dehydrating agent include phosphorus pentoxide and the like. The reaction solvent is not specifically limited as long as it does not significantly inhibit the reaction. Examples of preferred reaction solvents include, for example, dichloromethane, dichloroethane and the like. Further, the reaction solvent may not be used. Although the reaction temperature is not specifically limited, for example, from 0° C. to 100° C. is preferred. The reaction time is preferably from 1 to 24 hours.

<Step 11>

In step 11, compound (II) is produced by reacting compound (XIII) with a halogenating agent. Examples of the halogenating agent include N-chlorosuccinic imide, N-bromosuccinic imide, N-iodosuccinic imide, benzyltrimethylammonium tribromide and the like. This reaction can be accelerated by using a suitable acid. The reaction solvent is not specifically limited as long as it does not significantly inhibit the reaction. Examples of preferred reaction solvents include tetrahydrofuran, dichloromethane, dichloroethane and the like. Although the reaction temperature is not specifically limited, for example, from 0° C. to 100° C. is preferred. The reaction time is preferably from 1 to 72 hours.

Production Method-2 (Production Method Using an Asymmetric Element)

Compound (+)-(I) can also be produced with a method denoted in Scheme 4 recited below (Step 12 to Step 15).

Scheme 4

[Formula 8]

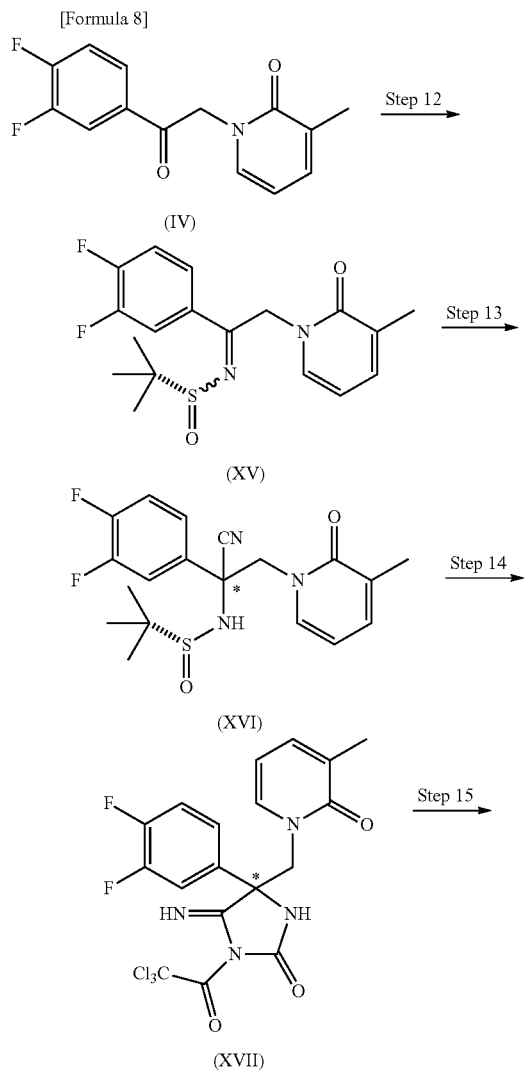

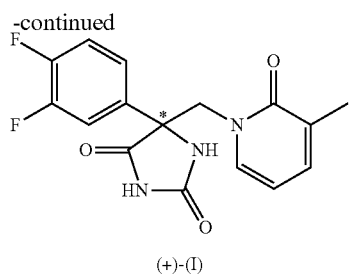

(wherein the asterisk (*) denotes being an optically pure form.)

<Step 12>

In step 12, compound (IV) is reacted with (R)-tert-butanesulfinamide to produce compound (XV). This reaction can be promoted by using an appropriate acid. As the acid, titanium tetraisopropoxide, titanium tetraethoxide, titanium tetrabutoxide, p-toluene sulfonic acid and the like are recited. The reaction solvent is not specifically limited as long as it does not significantly inhibit the reaction. Examples of preferred reaction solvents include, for example, toluene, xylene, benzene, tetrahydrofuran, dimethoxyethane, 1,4-dioxane and the like. The reaction temperature is not specifically limited. For example, 0° C. to 130° C. is preferred. The reaction time is preferably from 1 hour to 72 hours. The compound (XV) obtained in the present step is obtained in the E-form, Z-form or as a mixture thereof.

<Step 13>

In Step 13, compound (XV) is reacted with a cyaniding agent to produce compound (XVI). As the cyaniding agent, sodium cyanide, potassium cyanide, trimethylsilyl cyanide and the like are recited. This reaction can be promoted a Lewis acid or cation capturing agent. As the Lewis acid, trimethylaluminium and the like are recited. As the cation capturing agent, crown ether (15-crown-5,18-crown-6 and the like), hexamethylphosphoric triamide, N,N'-dimethylpropylene urea and the like are recited. The reaction solvent is not specifically limited as long as it does not significantly inhibit the reaction. Examples of preferred reaction solvents include, for example, toluene, xylene, benzene, tetrahydrofuran, dimethoxyethane, 1,4-dioxane and the like. The reaction temperature is not specifically limited. For example, −40° C. to 60° C. is preferred. The reaction time is preferably from 1 hour to 120 hours.

If necessary, step 12 to step 13 can be, without carrying out any specific treatments after the reactions, conducted in a one-pot manner.

<Step 14>

In Step 14, compound (XVI) is reacted, after removal of the tert-butylsulphinyl group using an acid, with isocyanic acid trichloroacetyl ester followed by treatment with triethylamine to produce compound (XVII). As the acid, hydrochloride, sulfuric acid, trifluoroacetic acid and the like are recited. The reaction solvent is not specifically limited as long as it does not significantly inhibit the reaction. Examples of preferred reaction solvents include, for example, methylene chloride, chloroform, toluene, xylene, benzene, tetrahydrofuran, dimethoxyethane, 1,4-dioxane and the like. The reaction temperature is not specifically limited. For example, 0° C. to 60° C. is preferred. The reaction time is preferably from 1 hour to 72 hours.

<Step 15>

In Step 15, compound (XVII) is hydrolyzed using an acid to produce compound (+)-(I). As the acid, hydrochloride, sulfuric acid, hydrobromic acid and the like are recited. The reaction solvent is not specifically limited as long as it does not significantly inhibit the reaction. Examples of preferred reaction solvents include, for example, methylene chloride, chloroform, toluene, xylene, benzene, tetrahydrofuran, dimethoxyethane, 1,4-dioxane, water and the like; this step can be carried out without an solvent. The reaction temperature is not specifically limited. For example, 0° C. to 120° C. is preferred. The reaction time is preferably from 1 hour to 72 hours.

The (+)-5-(3,4-difluorophenyl)-5-[(3-methyl-2-oxopyridin-1(2H)-yl)methyl]imidazolidine-2,4-dione (may be referred to as "the inventive compound") produced based on the above-described methods is isolated and purified as a free compound, a salt thereof, a hydrate thereof, a various solvate thereof such as ethanol solvate, polymorphilic crystalline products or the like. A pharmaceutically acceptable salt of the inventive compound can be prepared by a conventional salt-forming reaction. The isolation and purification can be carried out employing chemical operations such as fractional extraction, crystallization, and chromatography for fraction.

The (+)-5-(3,4-difluorophenyl)-5-[(3-methyl-2-oxopyridin-1(2H)-yl)methyl]imidazolidine-2,4-dione, or a salt thereof, according to the present invention exhibits an excellent selective TACE inhibitory effect, and can be used as the active ingredient of a pharmaceutical. Therefore, in view of the fact that the present invention also relates to a pharmaceutical that includes as the active ingredient (+)-5-(3,4-difluorophenyl)-5-[(3-methyl-2-oxopyridin-1(2H)-yl)methyl]imidazolidine-2,4-dione, or a salt thereof, based on the TACE inhibitory effect of the above-described (+)-5-(3,4-difluorophenyl)-5-[(3-methyl-2-oxopyridin-1(2H)-yl)methyl]imidazolidine-2,4-dione, or a salt thereof, the pharmaceutical according to the present invention is especially useful as a soluble TNF-α production inhibitor, and is also especially useful as a preventive or therapeutic agent for various kinds of TNF-α-related disease. Examples of such diseases include rheumatoid arthritis, psoriatic arthritis, systemic lupus erythematosus (SLE), lupus nephritis, systemic scleroderma, localized scleroderma, Sjogren's syndrome, polymyositis, dermatomyositis, ulcerative colitis, Crohn's disease, Behcet's disease, multiple sclerosis, arteriosclerosis, myasthenia gravis, ankylosing spondylitis, diabetes, sepsis, acute infectious diseases, asthma, chronic obstructive pulmonary disease (COPD), atopic dermatitis, contact dermatitis, psoriasis, acne, osteoporosis, burns, the onset of rejection associated with organs or tissue transplantation, fever, anemia, cancer, periodontal disease, glaucoma, diabetic complications, uveitis and the like. In addition, since the (+)-5-(3,4-difluorophenyl)-5-[(3-methyl-2-oxopyridin-1(2H)-yl)methyl]imidazolidine-2,4-dione, or a salt thereof, according to the present invention exhibits excellent pharmacological effects and transdermal absorption even when administered topically as illustrated in the below-described test examples 3 and 4, among TNF-α-related diseases, the pharmaceutical according to the present invention is especially useful as a preventive or therapeutic agent for diseases in which the symptoms appear on the skin (i.e. skin diseases). Examples of such skin diseases include localized scleroderma, atopic dermatitis, contact dermatitis, psoriasis, acne and the like.

The pharmaceutical containing (+)-5-(3,4-difluorophenyl)-5-[(3-methyl-2-oxopyridin-1(2H)-yl)methyl]imidazolidine-2,4-dione, or a salt thereof, according to the present invention may be administered systemically or locally, via an oral, transdermal, nasal, respiratory, pulmonary, ophthalmic, intravenous injection, subcutaneous injection, rectal administration method or the like. Further, the dosage form of this pharmaceutical can be appropriately selected in accordance with the administration route. Examples of such dosage form include a tablet, lozenge, sublingual tablet, sugar-coated tablet, capsule, pill, powder, granule, liquid, emulsion, cream, ointment, lotion, gel, jelly, suspension, syrup, eye drop, nasal drop, inhalant, suppository, adhesive (e.g. tape, film and the like), eye ointment, vaginal tablet, injection and the like.

Further, the present inventive pharmaceutical may appropriately contain a component other than the active ingredient ((+)-5-(3,4-difluorophenyl)-5-[(3-methyl-2-oxopyridin-1(2H)-yl)methyl]imidazolidine-2,4-dione, or a salt thereof), i.e. pharmaceutically acceptable liquid or solid additives for a formulations (e.g. excipient, binding agent, diluent, extender, disintegrator, stabilizer, preservative, buffering agent, emulsifier, fragrance, colorant, sweetener, thickener, corrigent, solubilizing agent or the like) and can be prepared according to a standard method in the present technical field.

Further, the present inventive (+)-5-(3,4-difluorophenyl)-5-[(3-methyl-2-oxopyridin-1(2H)-yl)methyl]imidazolidine-2,4-dione exhibits, as evidenced in Test Examples 5 and 6 recited hereinbelow, excellent solubility to an external base, so that, for the present inventive pharmaceutical, among the above mentioned various dosage forms, external formulations for transdermal administration; in the above mentioned various formulation forms, in a liquid, emulsion, cream, ointment, lotion, gel and the like, the present inventive compound as the active ingredient can be contained in a high content (e.g. 1 w/w % or higher) for a formulation with easy preparation. Among these external formulations, a lotion, cream, liquid or ointment is preferred.

Formulations in a form of external administration (external formulations) such as a liquid, emulsion, cream, ointment, lotion, gel and the like can be prepared in a standard manner in the present technical field. As bases used for the external formulations, with no specific limitations on pharmaceutically acceptable ones, a water-soluble base, oleaginous base, emulsion base are recited. One, two or more of these bases are used depending on necessity.

As the water-soluble base, for example, polyethylene glycol (macrogol), ethanol, glycerin, pharmaceutically acceptable glycols (e.g. propylene glycol, butylene glycol and the like) are recited. Among them, in terms of the present inventive compound's favorable solubility, pharmaceutically acceptable glycols are preferable.

As the oleaginous base, for example, Vaseline and paraffin, which are derived from mineral, plastibase, which is gelled polyethylene with liquid paraffin, bee wax, which is derived from living organisms and the like are recited.

As the emulsion base, for example, lanolin, stearyl alcohol and the like are recited. When an emulsion base is use, further addition of an emulsifier is preferable; as such emulsifiers, for example, polyoxyethylene hydrogenated caster oil, glycerol monostearate and the like are recited.

Furthermore, where necessary, various additives can be comprised. As the various additives, not specifically limited as long as they are pharmaceutically acceptable, for example, a film former such as alkyl methacrylate copolymer, hydroxypropyl cellulose, hydroxypropylmethyl cellulose, methyl cellulose, ethyl cellulose, polyvinyl alcohol and the like; a solvent such as water, ethyl acetate, butyl acetate, methyl ethyl ketone, adipic acid isopropyl ester, diethyl sebacate, triacetin and the like; and methyl parahydroxybenzoate (preservative), parahydroxybenzoic acid (preservative) and the like are recited.

The dose of the pharmaceutical containing (+)-5-(3,4-difluorophenyl)-5-[(3-methyl-2-oxopyridin-1(2H)-yl)methyl]imidazolidine-2,4-dione, or a salt thereof, according to the present invention may be appropriately determined based on conditions such as the administration target, the administration route, symptoms and the like. For example, for oral administration to an adult patient, the inventive compound, which is the active ingredient, may normally be administered in the range of about 0.01 to 100 mg/kg per dose, and preferably in the range of about 0.1 to 10 mg/kg, and it is preferred to administer from 1 to 3 times per day. Further, for example, in the case of applying on the skin of an adult patient as a topical agent, the inventive compound, which is the active ingredient, may normally be administered in the range of about 1 to 100,000 μg/cm$^2$ per day, preferably in the range of about 10 to 10,000 μg/cm$^2$, and more preferably in the range of about 10 to about 2,500 μg/cm$^2$, and it is preferred to administer once a day or a split into several times in one day.

In addition, in the pharmaceutical containing (+)-5-(3,4-difluorophenyl)-5-[(3-methyl-2-oxopyridin-1(2H)-yl)methyl]imidazolidine-2,4-dione, or a salt thereof, according to the present invention, as long as the active ingredient, (+)-5-(3,4-difluorophenyl)-5-[(3-methyl-2-oxopyridin-1(2H)-yl)methyl]imidazolidine-2,4-dione (may hereinbelow be referred to as "(+)-isomer") or a salt thereof, is contained at an effective amount, one which does substantially not contain (−)-5-(3,4-difluorophenyl)-5-[(3-methyl-2-oxopyridin-1(2H)-yl)methyl]imidazolidine-2,4-dione (may hereinbelow be referred to as "(−)-isomer") or a salt thereof is preferred. In this context, "substantially not contain the (−)-isomer" means that the (−)-isomer is undetectable or contained to the extent that it does not exert any medicinal action in vivo. The present invention also is related to a mixture (composition) consisting of the (+)-isomer and (−)-isomer; said mixture (composition) preferably is a mixture (composition) wherein 95 weight % or more of the (+)-isomer and 5 weight % or less of the (−)-isomer exist. Said mixture (composition) is, in a more preferred manner, a mixture (composition) wherein 98 weight % or more of the (+)-isomer and 2 weight % or less of the (−)-isomer exist, and further more preferably a mixture (composition) wherein 99.5 weight % or more of the (+)-isomer and 0.5 weight % or less of the (−)-isomer exist.

Still further, in the pharmaceutical containing (+)-5-(3,4-difluorophenyl)-5-[(3-methyl-2-oxopyridin-1(2H)-yl)methyl]imidazolidine-2,4-dione, or a salt thereof, according to the present invention, in the total amount of the 5-(3,4-difluorophenyl)-5-[(3-methyl-2-oxopyridin-1(2H)-yl)methyl]imidazolidine-2,4-dione or a salt thereof, the (+)-isomer preferably exists at 95 weight % or more (namely, the (+)-isomer exists at 90% ee or more), more preferred is one wherein the (+)-isomer exists at 98 weight % or more (namely, the (+)-isomer exists at 96% ee or more) and further more preferred is one wherein the (+)-isomer exists at 99.5 weight % or more (namely, the (+)-isomer exists at 99% ee or more).

EXAMPLES

Features of the present invention are described in more detail with reference to the following working examples and test examples. In the following examples and test examples, the materials, its usage amounts and ratios, handling, procedure or the like may be suitably modified as long as such modifications do not go beyond the intent of the invention. Therefore, the scope of the present invention should not be construed as being limited by the specific examples illustrated below.

The $^1$H-NMR spectra shown below were measured with a JNM-ECA 400 spectrometer (400 MHz, manufactured by JEOL, Ltd.) using deuterated chloroform (CDCl$_3$) or deuterated dimethyl sulfoxide (DMSO-d$_6$) as a solvent and tetramethylsilane (TMS) as an internal standard. In the chemical shift measurement results, the δ value is represented in ppm, and the coupling constant J value is represented in Hz. The abbreviation s stands for singlet, d for doublet, t for triplet, m for multiplet, and br for broad. For the mass spectrum (electrospray ionization: ESI-MS) measurement, Exactive manufactured by Thermo Fisher Scientific was employed. For the specific rotation measurement, a polarimeter SEPA-300 manufactured by HORIBA, Ltd. was employed.

Example 1

Production of (+)-5-(3,4-difluorophenyl)-5-[(3-methyl-2-oxopyridin-1(2H)-yl)methyl]imidazolidine-2,4-dione ((+)-(I))

Production by Production Method-1 (Production Method Using a Chiral Column)

[Formula 9]

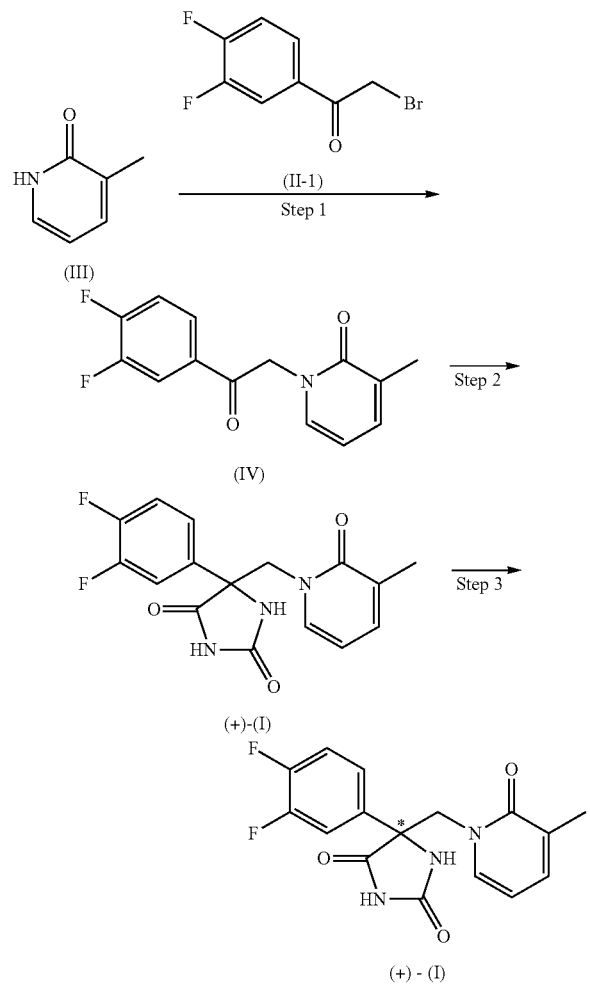

(wherein the asterisk (*) denotes being an optically pure form.)

Step 1

Cesium carbonate (436 mg, 1.3 mmol) and 3',4'-difluorophenacyl bromide (II-1) (300 mg, 1.3 mmol) were added to a solution of compound (III) (133 mg, 1.2 mmol) in N,N-dimethylformamide (10 mL), and the resultant mixture was stirred for 3 hours at room temperature. This reaction solution was diluted with water. The precipitated solid was collected by filtration and washed with water to obtain compound (IV) (amount 206 mg, yield 64%) as a yellow solid.

Step 2

Water (0.8 mL) was added to a suspension of the compound (IV) (206 mg, 0.78 mmol), potassium cyanide (61 mg, 0.94 mmol), and ammonium carbonate (301 mg, 3.13 mmol) in ethanol (0.8 mL). The resultant mixture was sealed, and stirred for 67 hours at 100° C. After leaving to cool, the reaction solution was diluted with water, and the mixture was extracted with ethyl acetate. The resultant product was dried over anhydrous sodium sulfate, and the solvent was removed under reduced pressure. Chloroform was added to the residue, and the precipitated solid was collected by filtration to obtain compound (±)-(I) (amount 119 mg, yield 46%) as a colorless solid. The physical properties are shown below.

$^1$H-NMR (DMSO-d$_6$) δ: 1.98 (3H, s), 4.46 (1H, d, J=13.7 Hz), 4.61 (1H, d, J=13.7 Hz), 6.13 (1H, t, J=6.9 Hz), 7.22-7.33 (2H, m), 7.45-7.58 (2H, m), 7.69 (1H, ddd, J=2.3, 7.8, 12.4 Hz), 8.66 (1H, s), 10.99 (1H, s).

MS (ESI-FTMS) m/z 334 [M+H]$^+$.

The compound (±)-(I) obtained by conducting Step 2 more than once was combined to provide for the succeeding Step 3.

Step 3

A high-performance liquid chromatography (LaChrom Elite, Hitachi High Technologies Corporation) was installed with a resolving column (CHIRALPAK AD), and n-hexane-ethanol (30:70) was passed through at column tenperature 40° C. with a flow rate 8 mL/min for one hour to equilibrate. A solution of the Compound (±)-(I) (14 mg) in n-hexane-ethanol (30:70, 2 mL) was injected and, under observation on a UV detector, the first peak (about 12.5 min. to 15.5 min.) and the second peak (about 18 min. to 23 min.) were each collected. After the similar procedure was repeated, each was evaporated of the solvent under reduced pressure. As the compound showing the first peak, the present inventive compound, (+)-5-(3,4-difluorophenyl)-5-[(3-methyl-2-oxopyridin-1(2H)-yl)methyl]imidazolidine-2,4-dione (yield 86 mg, optical purity >99.9% ee), was obtained. As the compound showing the second peak, enantiomer of the present compound, (−)-5-(3,4-difluorophenyl)-5-[(3-methyl-2-oxopyridin-1(2H)-yl)methyl]imidazolidine-2,4-dione (yield 84 mg, optical purity >99.8% ee), was obtained.

The physical properties of compound (+)-(I) are shown below:

HPLC retention time 14.4 minutes (analytical conditions, column: CHIRALPAK AD-H 4.6φ×250 mm, mobile phase: n-hexane:ethanol=40:60, flow rate: 0.5 mL/min, column temperature: 30° C., detection wavelength: 254 nm)

$[α]_D^{26.7}$=+229.9° (c 1.0, CHCl$_3$)

$^1$H-NMR (400 MHz, DMSO-d$_6$) δ: 1.98 (3H, s), 4.46 (1H, d, J=13.3 Hz), 4.60 (1H, d, J=13.3 Hz), 6.12 (1H, t, J=6.9 Hz), 7.25 (1H, d, J=6.9 Hz), 7.29 (1H, d, J=6.0 Hz), 7.45-7.58 (2H, m), 7.65-7.73 (1H, m), 8.63 (1H, s), 10.98 (1H, s).

MS (ESI-FTMS) m/z 334 [M+H]$^+$.

The physical properties of the enantiomer of the present compound, (+5-(3,4-difluorophenyl)-5-[(3-methyl-2-oxopyridin-1(2H)-yl)methyl]imidazolidine-2,4-dione, are shown below:

HPLC retention time 33.8 minutes (analytical conditions, column: CHIRALPAK AD-H 4.6φ×250 mm, mobile phase: n-hexane:ethanol=40:60, flow rate: 0.5 mL/min, column temperature: 30° C., detection wavelength: 254 nm)

$[α]_D^{27.3}$=−196.7° (c 1.0, CHCl$_3$)

$^1$H-NMR (400 MHz, DMSO-d$_6$) δ: 1.98 (3H, s), 4.46 (1H, d, J=13.7 Hz), 4.60 (1H, d, J=13.7 Hz), 6.12 (1H, t, J=6.7 Hz), 7.25 (1H, d, J=6.9 Hz), 7.29 (1H, d, J=6.4 Hz), 7.45-7.58 (2H, m), 7.69 (1H, ddd, J=2.3, 7.8, 12.4 Hz), 8.62 (1H, s), 10.98 (1H, s).

Production by Production Method-2 (Production Method Using an Asymmetrical Element)

[Formula 10]

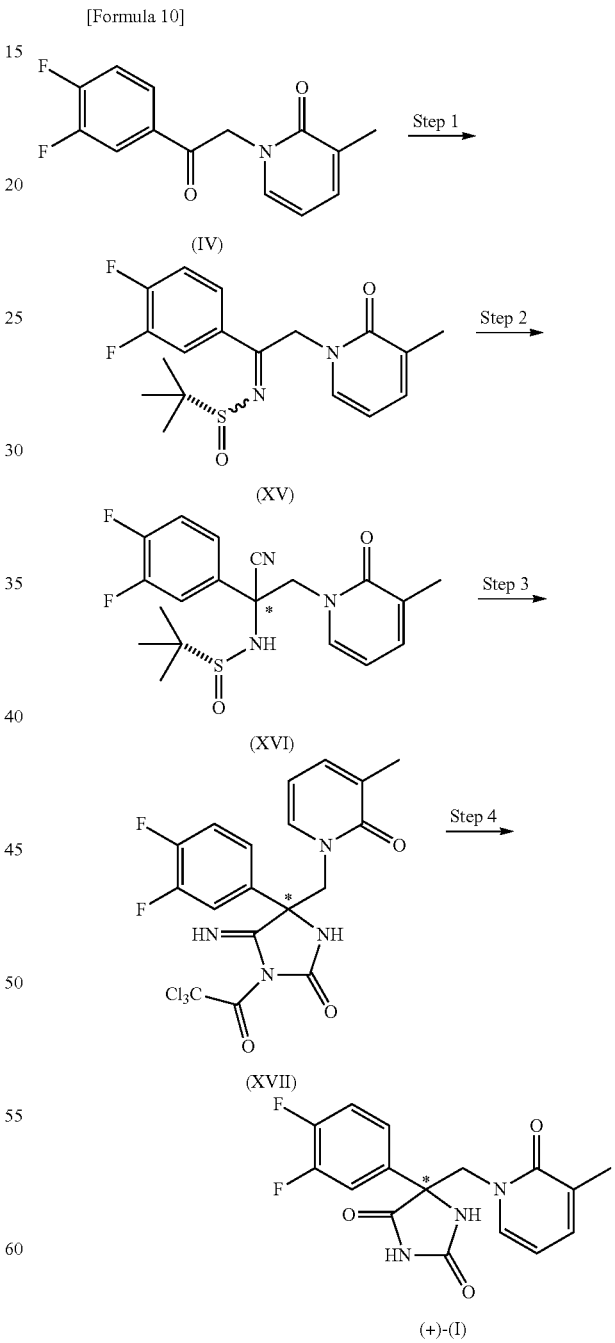

(wherein the asterisk (*) denotes being an optically pure form. In addition, the numbers on each step are those of the steps in the present Example.)

Step 1

To a solution of the compound (IV) (500 mg, 1.89 mmol) and (R)-tert-butanesulfinamide (345 mg, 2.85 mmol) in toluene (1.9 mL), titanium tetraisopropoxide (596 μL, 2.85 mmol) was added and stirred at 100° C. for 16 hours. After cooling to room temperature, a saturated ammonium chloride aqueous solution was added and stirred. Precipitated solid was filtered off by Celite filtration and washed with ethyl acetate. Organic layer was separated and washed with a saturated sodium chloride aqueous solution; dried over anhydrous sodium sulfate and the solvent was evaporated under reduced pressure. The residue was purified with column chromatography (silica gel) to obtain compound (XV) (amount 447 mg, yield 64%).

Step 2

Under cooling at −20° C., to a solution of the compound (XV) (244 mg, 0.67 mmol) in toluene (1.3 mL), a toluene solution (1.8 mol/L, 556 μL, 1.00 mmol) of trimethyl aluminium and trimethylsilyl cyanide (126 μL, 1.00 mmol) were added and stirred at −20° C. for 2 hours. A saturated ammonium chloride aqueous solution was added and precipitated solid was filtered off by Celite filtration and washed with ethyl acetate. Organic layer was separated and washed with a saturated sodium chloride aqueous solution; dried over anhydrous sodium sulfate and the solvent was evaporated under reduced pressure. The residue was purified with column chromatography (silica gel) to obtain compound (XVI) (amount 145 mg, yield 55%).

$^1$H-NMR (400 MHz, CDCl$_3$) δ: 1.27 (9H, s), 2.18 (3H, s), 4.02 (1H, d, J=13.7 Hz), 4.80 (1H, d, J=13.7 Hz), 6.21 (1H, t, J=6.9 Hz), 7.04 (1H, m), 7.30 (1H, m), 7.40-7.50 (2H, m).

Step 3

Under ice cooling, to a solution of the compound (XVI) (130 mg, 0.337 mmol) in ethyl acetate (3.3 mL), a hydrochloride-ethyl acetate solution (1.5 mL) was added and stirred for 30 minutes. The reaction solution was concentrated under reduced pressure, and dissolved in methylene chloride (3.3 mL). To the solution was added isocyanic acid trichloroacetyl ester (47 μL, 0.40 mmol) and the solution was stirred at room temperature for 40 minutes. To the reaction mixture, triethyl amine (46 μL, 0.33 mmol) was added and stirred at room temperature for 2 hours. The reaction solution was concentrated under reduced pressure and the residue was purified with column chromatography (silica gel) to obtain compound (XVII) (amount 142 mg, yield 90%).

$^1$H-NMR (400 MHz, CDCl$_3$) δ: 2.23 (3H, s), 4.00 (1H, d, J=14.2 Hz), 5.07 (1H, d, J=14.2 Hz), 6.20 (1H, t, J=6.9 Hz), 7.16 (1H, m), 7.22-7.33 (2H, m), 7.37-7.51 (2H, m), 8.75 (1H, s), 10.17 (1H, s).

Step 4

The compound (XVII) (125 mg, 0.26 mmol) was added with 6 mol/L hydrochloride (5.2 mL) and stirred at 100° C. for 16 hours. After cooled to room temperature, the reaction solution was diluted with water and extracted twice with ethyl acetate. The organic layers were combined, washed with a saturated sodium chloride aqueous solution, dried over sodium sulfate and the solvent was evaporated under reduced pressure. The residue was purified with column chromatography (silica gel) to obtain (+)-(I) (amount 80 mg, yield 92%, optical purity 97.6% ee) as colorless solid.

$[α]_D^{26.5}$=+229.6° (c 0.05, CHCl$_3$)

H-NMR (400 MHz, DMSO-d$_6$) δ: 1.98 (3H, s), 4.46 (1H, d, J=13.7 Hz), 4.58 (1H, d, J=13.7 Hz), 6.12 (1H, t, J=6.9 Hz), 7.22-7.33 (2H, m), 7.45-7.58 (2H, m), 7.69 (1H, ddd, J=2.3, 7.8, 12.4 Hz), 8.51 (1H, s), 10.99 (1H, s).

Test Example 1

TACE Inhibition Test (In Vitro)

The nucleotide sequence of TACE has been reported by Moss et al. (Moss, M. L. et al., Nature 1997, 385, 733-736). Accordingly, the cDNA of TACE was obtained according to the prescribed method from THP-1 cells or the like, and then incorporated the cDNA into an expression vector. Next, this vector was transformed into mammalian cells or insect cells, and TACE expression was obtained.

The TACE inhibition test was carried out by measuring TACE activity in the presence and the absence of the test substance using the thus-obtained TACE as an enzyme, and a fluorescent synthetic substrate Nma(N-methylanthranilic acid)-Leu-Ala-Gln-Ala-Val-Arg-Ser-Ser-Lys(Dnp(dinitrophenyl))-D-Arg-NH$_2$ (SEQ ID NO: 1) including the TACE-cleaved sequence of a membrane-bound TNF as a substrate. The TACE inhibition test method is shown below.

Namely, 90 μL of an enzyme solution prepared with an assay buffer A (50 mM tris-hydrochloric acid buffer (pH 7.5) including 200 mM sodium chloride, 5 mM calcium chloride, 10 μM zinc sulfate, and 2 mg/mL bovine serum albumin) and 90 μL of a fluorescent synthetic substrate prepared with an assay buffer B (50 mM tris-hydrochloric acid buffer (pH 7.5) including 200 mM sodium chloride, 5 mM calcium chloride, 10 μM zinc sulfate, and 0.05% PLURONIC F-68) were mixed together, and reacted at 37° C. for 1.5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration (IC$_{50}$) of the test substance was calculated.

According to the result, the present inventive (+)-5-(3,4-difluorophenyl)-5-[(3-methyl-2-oxopyridin-1(2H)-yl)methyl]imidazolidine-2,4-dione exhibited a TACE inhibitory activity of 100 nM or less of IC$_{50}$ value.

Test Example 2

MMP Inhibition Tests

MMP inhibition tests can be carried out, for example, using a fluorescent synthetic substrate based on the methods described in Bickett et al. (D. Mark Bickett et al., Anal. Biochem., 1993, 212, 58-64) and Nagase et al. (H. Nagase et al., J. Biol. Chem., 1994, 269, 20952-20957). The method for each MMP inhibition test is shown below.

MMP-1 Inhibition Test

180 μL (100 ng) of human MMP-1 (Calbiochem #444208) was mixed with 20 μL of 10 mM p-amino phenyl mercuric acetate (APMA), and activated by reacting at 37° C. for 1 hour. 20 μL of the resultant enzyme solution was diluted to 90 μL with an assay buffer A. The mixture was added to 90 μL of a 20 μM fluorescent substrate (Dnp-Pro-Cha(β-cyclohexylalanyl)-Gly-Cys(Me)-His-Ala-Lys(Nma)-NH$_2$) (SEQ ID NO: 2) prepared with an assay buffer B, and reacted at 37° C. for 5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration ($IC_{50}$) of the test substance was calculated.

MMP-2 Inhibition Test

90 μL (5 ng) of human MMP-2 (Calbiochem #444213) was mixed with 10 μL of 10 mM APMA, and activated by reacting at 37° C. for 1 hour. 10 μL of the resultant enzyme solution was diluted to 90 μL with an assay buffer A. The mixture was added to 90 μL of a 20 μM fluorescent substrate (MOCAc((7-methoxycoumarin-4-yl)acetyl)-Pro-Leu-Gly-Leu-$A_2$pr(Dnp)-Ala-Arg-$NH_2$, Peptide Institute Inc., #3163-v) (SEQ ID NO: 3) prepared with an assay buffer B, and reacted at 37° C. for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration ($IC_{50}$) of the test substance was calculated.

MMP-3 Inhibition Test

90 μL (1.5 ng) of human MMP-3 (Calbiochem #444217) prepared with an assay buffer A was added to 90 μL of a 20 μM fluorescent substrate NFF-3 (MOCAc((7-methoxycoumarin-4-yl)acetyl)-Arg-Pro-Lys-Pro-Val-Glu-Nva-Trp-Arg-Lys(Dnp)-$NH_2$, Peptide Institute Inc., #3168-v) (SEQ ID NO: 4) prepared with an assay buffer B, and reacted at 37° C. for 4 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration ($IC_{50}$) of the test substance was calculated.

MMP-8 Inhibition Test

90 μL (29 ng) of human MMP-8 (Calbiochem #444229) was mixed with 10 μL of 10 mM APMA, and activated by reacting at 37° C. for 1 hour. 10 μL of the resultant enzyme solution was diluted to 90 μL with an assay buffer A. The mixture was added to 90 μL of a 20 μM fluorescent substrate (MOCAc-Pro-Leu-Gly-Leu-$A_2$pr(Dnp)-Ala-Arg-$NH_2$, Peptide Institute Inc., #3163-v) (SEQ ID NO: 3) prepared with an assay buffer B, and reacted at 37° C. for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitiory concentration ($IC_{50}$) of the test substance was calculated.

MMP-9 Inhibition Test

90 μL (11 ng) of human MMP-9 (Calbiochem #444231) was mixed with 10 μL of 10 mM APMA, and activated by reacting at 37° C. for 2 hours. 10 μL of the resultant enzyme solution was diluted to 90 μL with an assay buffer A. The mixture was added to 90 μL of a 20 μM fluorescent substrate (Dnp-Pro-Cha-Gly-Cys(Me)-His-Ala-Lys(Nma)-$NH_2$) (SEQ ID NO: 2) prepared with an assay buffer B, and reacted at 37° C. for 4 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration ($IC_{50}$) of the test substance was calculated.

MMP-13 Inhibition Test

90 μL (130 ng) of human MMP-13 (Calbiochem #444287) was mixed with 10 μL of 10 mM APMA, and activated by reacting at 37° C. for 1 hour. 10 μL of the resultant enzyme solution was diluted to 90 μL with an assay buffer A. The mixture was added to 90 μL of a 20 μM fluorescent substrate (Dnp-Pro-Cha-Gly-Cys(Me)-His-Ala-Lys(Nma)-$NH_2$) (SEQ ID NO: 2) prepared with an assay buffer B, and reacted at 37° C. for 4 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration ($IC_{50}$) of the test substance was calculated.

MMP-14 Inhibition Test

90 μL (1.9 ng) of human MMP-14 (Calbiochem #475935) prepared with an assay buffer A was added to 90 μL of a 20 μM fluorescent substrate (Dnp-Pro-Cha-Gly-Cys(Me)-His-Ala-Lys(Nma)-$NH_2$) (SEQ ID NO: 2) prepared with an assay buffer B, and reacted at 37° C. for 5 hours. Enzyme activity was then determined by measuring with a fluorescence intensity meter (Labsystems, Fluoroskan Ascent) at an excitation wavelength of 355 nm and a measurement wavelength of 460 nm.

From the enzyme activity in the presence or the absence of the test substance, the inhibition rate was determined, and the 50% inhibitiory concentration ($IC_{50}$) of the test substance was calculated.

MMP-17 Inhibition Test

90 μL (5.8 ng) of human MMP-17 (Calbiochem #475940) prepared with an assay buffer A was added to 90 μL of a 20 μM fluorescent substrate (MOCAc-Pro-Leu-Gly-Leu-$A_2$pr(Dnp)-Ala-Arg-$NH_2$, Peptide Institute Inc., #3163-v) (SEQ ID NO: 3) prepared with an assay buffer B, and reacted at room temperature for 5 hours. Enzyme activity was then determined by measuring with a fluorescence intensity meter (Labsystems, Fluoroskan Ascent) at an excitation wavelength of 320 nm and a measurement wavelength of 405 nm.

From the enzyme activity in the presence or the absence of the test substance, the inhibition rate was determined, and the 50% inhibitory concentration ($IC_{50}$) of the test substance was calculated.

As obtained in these tests, 50% inhibitory concentrations against MMPs of the present inventive (+)-5-(3,4-difluorophenyl)-5-[(3-methyl-2-oxopyridin-1(2H)-yl)methyl]imidazolidine-2,4-dione, are shown in Table 1.

TABLE 1

| | Inhibitory activity ($IC_{50}$, nM) |
|---|---|
| MMP-1 | >10000 |
| MMP-2 | >10000 |
| MMP-3 | >10000 |
| MMP-8 | >10000 |
| MMP-9 | >10000 |
| MMP-13 | >10000 |
| MMP-14 | >10000 |
| MMP-17 | >10000 |

Test Example 3

Inhibition Test of Auricular Oedema Induced by Single Application of TPA (12-O-Tetradecanoylphorbol-13-Acetate) in Mouse (In Vivo Efficacy Test Based on TNF-α-Related Cutaneous Inflammation)

Auricular oedema was induced by applying 54 µmol/L TPA-acetone solution on both the inner and outer sides of the left ear of BALB/c mice (application volume of 54 µmol/L TPA-acetone solution is 10 µL for each side of the left ear (i.e. 1.08 nmol TPA/auricle)). For a non-induced group, acetone was similarly applied instead of the 54 µmol/L TPA-acetone solution. The test substance was dissolved and prepared in a 1 w/v % solution of acetone containing 10 vol % DMSO (topical administration vehicle), then the test solution was applied onto both the inner and outer sides of the left ear of the mice (application volume of this test solution is 10 µL for each side of the left ear) 1 hour before the TPA application. For a control group, the topical administration vehicle was similarly applied instead of the test substance solution. For an etanercept group, 0.2 mL of a 5 mg/mL etanercept solution was intravenously administered (1 mg/mouse) the day before TPA application and 1.5 hours before TPA application. For a human IgG (hIgG) group (etanercept control group), 0.2 mL of a 5 mg/mL hIgG solution was intravenously administered (1 mg/mouse). Auricle thickness was measured under ether anesthesia the day before TPA application and 6 hours after TPA application for evaluation of the auricular oedema inhibition effect of the test substance based on the increase in auricle thickness as an index.

The auricular oedema inhibition rate (%) of the test substance was calculated based on the following formula using (A) the average value of the increase in auricular thickness of the group administered with the test substance, (B) the average value of the increase in auricular thickness of the non-induced group, and (C) the average value of the increase in auricular thickness of the control group.

Auricular oedema inhibition rate (%) of the test substance=$(C-A)/(C-B) \times 100$ (A): Average value of the increase in auricular thickness of the group administered with the test substance
(B): Average value of the increase in auricular thickness of the non-induced group
(C): Average value of the increase in auricular thickness of the control group The auricular oedema inhibition rate (%) of etanercept was calculated based on the following formula using (B) the average value of the increase in auricular thickness of the non-induced group, (D) the average value of the increase in auricular thickness of the etanercept group, and (E) the average value of the increase in auricular thickness of the hIgG group.

Auricular oedema inhibition rate (%) of etanercept=$(E-D)/(E-B) \times 100$ (D): Average value of the increase in auricular thickness of the etanercept group
(E): Average value of the increase in auricular thickness of the hIgG group Further, etanercept ratio was calculated based on the following formula by comparing the auricular oedema inhibition rate (%) of the test substance with the auricular oedema inhibition rate (%) of etanercept (used as positive control) at the same time.

"Etanercept ratio"=Auricular oedema inhibition rate (%) of each test substance/auricular oedema inhibition rate (%) of etanercept The auricular oedema inhibition rate (%) of the present inventive (+)-5-(3,4-difluorophenyl)-5-[(3-methyl-2-oxopyridin-1(2H)-yl)methyl]imidazolidine-2,4-dione was 62% and the etanercept ratio was 3.4.

The compound according to the present invention exhibited a superior effect by topical administration than the intravenous administration of etanercept, which is a commercially available drug for TNF-α related diseases.

Test Example 4

Pharmacokinetic Study after Intravenous and Percutaneous Administration in Hairless Mice Intravenous Administration
Test substances (0.1 to 0.5 mg/5 mL/kg) were administered by bolus injection into the tail vein of hairless mice under anesthesia.

Percutaneous Administration
A 4 cm$^2$ administration site (2 cm×2 cm) was marked on the back skin of hairless mice under anesthesia (fed) using an oil-based marker. Test substances were applied to the administration site at 50 µL/animal (1 w/v % Macrogol 400 solution). Gauze (BEMCOT®) about 2 cm×2 cm in size was fixed using double-sided tape to an approximately 4 cm×4 cm polyethylene sheet, and the gauze face was placed over the face on which the test substance had been applied. An adhesive elastic bandage (Elastopore, about 10 cm) was stuck over the gauze to fix and protect the face on which the test substance had been applied. The mice were then returned to its cage. Twenty-four hours after administration, occlusive application was confirmed to have been properly carried out.

Blood Collection
The tail vein of mice was cut with a razor, and blood was collected from the tail vein using a micropipette. The blood samples were collected 5, 15, 30 minutes, 1, 3, and 6 hours after intravenous administration, and 30 minutes, 1, 3, 6, and 24 hours after percutaneous administration, respectively. The amount of blood collected at each point was about 30 to 50 µL. The blood was transferred to a tube containing heparin sodium, and the plasma was obtained by centrifugation (4° C., 19,200×g, 10 min). The plasma was cryopreserved in a freezer with a set temperature of −30° C.

Method for Measuring Plasma Concentration of Test Substance
The cryopreserved plasma obtained by the above method was thawed at room temperature. After removing the protein using methanol, the concentration of the test substance in the plasma was measured. The instruments used for the measurement of the plasma concentration were consisted of HTC PAL autosampler manufactured by CTC Analytics, and an Accela HPLC and a TSQ Quantum Ultra manufactured by Thermo Fisher Scientific.

Calculation of Transdermal Absorption Rate
Transdermal absorption rate was calculated using the following equation by calculating the AUC (area under the curve of the concentration in plasma) from the plasma concentration of the test substance measured by the method described above.

Transdermal absorption rate (%)=$((Div \times AUCpc)/(Dpc \times AUCiv)) \times 100$ Div: Dose of test substance during intravenous administration Dpc: Dose of test substance during percutaneous administration AUCiv: Area under the curve of the plasma concentration of the test substance after intravenous administration AUCpc: Area under the curve of the plasma concentration of the test substance after percutaneous administration It was confirmed that the compound according to the present invention has good transdermal absorbability after percutaneous administration. Therefore, it is inferred that the compound according to the present invention also has good skin permeability.

Test Example 5

Solubility Test in the 2nd Fluid for the Disintegration Test of the Japanese Pharmacopoeia Preparation of a Sample Solution for a Calibration Curve Test substances (10.0 mg) were correctly weighed, and methanol was added to adjust to 10 mL. The solution was diluted by 10 times to prepare a solution of 100 mg/mL.
Preparation of a Sample Solution for Solubility Measurement In a centrifuge tube 5.0 mg of the test substance was weighed, added with 5.0 mL of the 2nd fluid for the disintegration test of the Japanese pharmacopoeia, supersonified for 3 minutes, and shaken for 2 hours thereafter. This solution was filitered with a membrane filter (0.2 μm), 500 μL the filtrate was measured, 500 μL of acetonitrile was added, and fully stirred to obtain the sample solution.
Preparation of the 2nd Fluid for the Disintegration Test of the Japanese Pharmacopoeia (pH6.8)

To 250 mL of 0.2 mol/L potassium dihydrogenphosphate aqueous solution, 118 mL of 0.2 mol/L sodium hydroxide aqueous solution and water was added to adjust to 1000 mL.
Measuring Method of Solubility in the 2nd Fluid for the Disintegration Test of the Japanese Pharmacopoeia Using a high performance liquid chromatography, each of the sample solution for a calibration curve and sample solution for solubility measurement is measured twice to calculate an average area for each.
Calculation Method of Solubility in the 2nd Fluid for the Disintegration Test of the Japanese Pharmacopoeia Based on the average area obtained in the above mentioned method, using an equation below to calculate a solubility.

Solubility in the 2nd fluid for the disintegration test of the Japanese pharmacopoeia(μg/mL)=((P×2)/S)×100

S: Average area on the sample solution for a calibration curve

P: Average area on the sample solution for solubility measurement

The solubility (μg/mL) in the 2nd fluid for the disintegration test of the Japanese pharmacopoeia, obtained in the test, of the present inventive (+)-5-(3,4-difluorophenyl)-5-[(3-methyl-2-oxopyridin-1(2H)-yl)methyl]imidazolidine-2,4-dione and the reference compound, (±)-5-(3,4-difluorophenyl)-5-[(3-methyl-2-oxopyridin-1(2H)-yl)methyl]imidazolidine-2,4-dione, is shown in Table 2.

TABLE 2

|  | Solubility in the 2nd fluid for the disintegration test of the Japanese pharmacopoeia (μg/mL) |
| --- | --- |
| (+)-5-(3,4-difluorophenyl)-5-[(3-methyl-2-oxopyridin-1(2H)-yl)methyl]imidazolidine-2,4-dione | 430 |
| (±)-5-(3,4-difluorophenyl)-5-[(3-methyl-2-oxopyridin-1(2H)-yl)methyl]imidazolidine-2,4-dione | 45 |

With the test, the present inventive compound has, in comparison with the racemate thereof, remarkably higher solubility in the 2nd fluid for the disintegration test of the Japanese pharmacopoeia. The present inventive compound hence clearly has an advantageous feature in preparing a formulation.

Test Example 6

Solubility Test in Organic Solvents

Under room temperature conditions, in a 0.5 mL polypropylene tube, (+)-5-(3,4-difluorophenyl)-5-[(3-methyl-2-oxopyridin-1(2H)-yl)methyl]imidazolidine-2,4-dione and (±)-5-(3,4-difluorophenyl)-5-[(3-methyl-2-oxopyridin-1 (2H)-yl)methyl]imidazolidine-2,4-dione measured in advance for a suitable amount were prepared, respectively. In each tube, solvent (Propylene glycol (PG) or butylene glycol (BG)) was added with various amounts, e.g. 10 times, 20 times or 100 times amount of the test compound, and stirred with a vortex mixer. With a table ultrasonic washer set at 37° C., ultrasonication treatment was given for 10 minutes; after warming for an hour in a thermostat chamber, each were kept standing for 24 hours at room temperature. The test solutions were observed by sight to evaluate the states in accordance with the determination criterion given below.
Determination Criterion on Solubility in Solvents Determination criterion consisted of the following two categories:

"Soluble": Test compound dissolved; no undissolved substances confirmed by visual observation.

"Insoluble": Test compound remains undissolved; undissolved substances confirmed by visual observation.

Table 3 shows the result of the solubility test for the present inventive (+)-5-(3,4-difluorophenyl)-5-[(3-methyl-2-oxopyridin-1(2H)-yl)methyl]imidazolidine-2,4-dione and, the reference compound, (±)-5-(3,4-difluorophenyl)-5-[(3-methyl-2-oxopyridin-1(2H)-yl)methyl]imidazolidine-2,4-dione.

TABLE 3

|  |  | (+)-5-(3,4-difluorophenyl)-5-[(3-methyl-2-oxopyridin-1(2H)-yl)methyl]imidazolidine-2,4-dione | (±)-5-(3,4-difluorophenyl)-5-[(3-methyl-2-oxopyridin-1(2H)-yl)methyl]imidazolidine-2,4-dione |
| --- | --- | --- | --- |
| PG | 100 times amount | Soluble | Soluble |
|  | 20 times amount | Soluble | Insoluble |
|  | 10 times amount | Soluble | Insoluble |
| BG | 100 times amount | Soluble | Soluble |
|  | 20 times amount | Soluble | Insoluble |

With the above mentioned test, the present inventive compound was confirmed to have a higher solubility in glycol solvents compared with its racemate. The present inventive compound hence clearly has an advantageous feature in preparing a formulation using a water-soluble base.

The results obtained in Test Examples 5 and 6 clearly show that the present inventive compound has a remarkably high solubility in a water-soluble base or water widely used in general as bases. The present inventive compound, having such a high solubility, achieves very easy preparation of external formulations of high concentrations such as the content of 1 w/w % or more of said compound as an active ingredient.

Explanation is given hereinbelow on formulation Examples of pharmaceuticals having as an active ingredient the present inventive compound with specific examples. Materials, its usage amounts and ratios, methods, procedures and the like in the following Formulation Examples can be modified as long as the purpose of the present invention is kept. The scope of the present invention should hence not be construed in a limited manner with the following specific examples.

Formulation Example 1

1 w/w % Ointment

Dose in 1 g of Ointment
(1) Compound (+)-(I) 10 mg
(2) White petroleum 990 mg
(1) and (2) are melt-blended under heating on water (80° C.), and stirred for uniformity under cooling until solidified to prepare.

Formulation Example 2

3 w/w % Ointment

Dose in 1 g of Ointment
(1) Compound (+)-(I) 30 mg
(2) White petroleum 970 mg
(1) and (2) are melt-blended under heating on water (80° C.), and stirred for uniformity under cooling until solidified to prepare.

Formulation Example 3

1 w/w % Cream

Dose in 1 g of Cream
(1) Compound (+)-(I) 10 mg
(2) White petroleum 250 mg
(3) Stearyl alcohol 200 mg
(4) Propylene glycol 120 mg
(5) Polyoxyethylene hydrogenated caster oil 40 mg
(6) Glycerol monostearate 10 mg
(7) Methyl paraoxybenzoate 1 mg
(8) Propyl paraoxybenzoate 1 mg
(9) Purified water Suitable amount
(1) to (3) are melt-blended under heating on water (80° C.), added with a solution heated to 80° C. in which (4) to (8) were dissolved in advance in purified water, and stirred for uniformity under cooling until solidified to prepare.

Formulation Example 4

3 w/w % Cream

Dose in 1 g of Cream
(1) Compound (+)-(I) 30 mg
(2) White petroleum 250 mg
(3) Stearyl alcohol 200 mg
(4) Propylene glycol 120 mg
(5) Polyoxyethylene hydrogenated caster oil 40 mg
(6) Glycerol monostearate 10 mg
(7) Methyl paraoxybenzoate 1 mg
(8) Propyl paraoxybenzoate 1 mg
(9) Purified water Suitable amount
(1) to (3) are melt-blended under heating on water (80° C.), added with a solution heated to 80° C. in which (4) to (8) were dissolved in advance in purified water, and stirred for uniformity under cooling until solidified to prepare.

Formulation Example 5

Tablet

Dose in 1 g of Tablet
(1) Compound (+)-(I) 100 mg
(2) Lactose 308 mg
(3) Carboxymethyl-cellulose calcium 30 mg
(4) Hydroxymethyl-cellulose 7 mg
(5) Magnesium stearate 5 mg
(6) Microcrystalline cellulose 50 mg
(1) to (4) and (6) are mixed for uniformity, and granulation and sieving is conducted. (5) is added and mixed together, and compressed thereafter to prepare.

Formulation Example 6

1 w/w % Liquid

Dose in 1 g of Liquid
(1) Compound (+)-(I) 10 mg
(2) Ethanol 500 mg
(3) Glycerin 200 mg
(4) Propylene glycol 200 mg
(5) Purified water Suitable amount
Stir (1) to (5) to prepare.

Formulation Example 7

3 w/w % Liquid

Dose in 1 g of Liquid
(1) Compound (+)-(I) 30 mg
(2) Ethanol 500 mg
(3) Glycerin 200 mg
(4) Propylene glycol 200 mg
(5) Purified water Suitable amount
Stir (1) to (5) to prepare.

Formulation Example 8

1 w/w % Emulsion Lotion

Dose in 1 g of Lotion
(1) Compound (+)-(I) 10 mg
(2) White petroleum 250 mg
(3) Stearyl alcohol 50 mg
(4) Propylene glycol 120 mg
(5) Polyoxyethylene hydrogenated caster oil 40 mg
(6) Glycerol monostearate 10 mg
(7) Methyl paraoxybenzoate 1 mg
(8) Propyl paraoxybenzoate 1 mg
(9) Purified water Suitable amount (1) to (3) are melt-blended under heating on water (80° C.), added with a solution heated to 80° C. in which (4) to (8) were dissolved in advance in purified water, and stirred under cooling to prepare.

Formulation Example 9

3 w/w % Emulsion Lotion

Dose in 1 g of Lotion
(1) Compound (+)-(I) 30 mg
(2) White petroleum 250 mg
(3) Stearyl alcohol 50 mg
(4) Propylene glycol 120 mg
(5) Polyoxyethylene hydrogenated castor oil 40 mg
(6) Glycerol monostearate 10 mg
(7) Methyl paraoxybenzoate 1 mg
(8) Propyl paraoxybenzoate 1 mg
(9) Purified water Suitable amount (1) to (3) are melt-blended under heating on water (80° C.), added with a solution heated to 80° C. in which (4) to (8) were dissolved in advance in purified water, and stirred under cooling to prepare.

INDUSTRIAL APPLICABILITY (+)-5-(3,4-difluorophenyl)-5-[(3-methyl-2-oxopyridin-1 (2H)-yl)methyl]imidazolidine-2,4-dione, or a salt thereof has excellent selective TACE inhibitory function, so that it is useful as an active ingredient in a pharmaceutical for treating and preventing TNF-α-relate diseases.

The invention claimed is:

1. (+)-5-(3,4-Difluorophenyl)-5-[(3-methyl-2-oxopyridin-1(2H)-yl)methyl]imidazolidine-2,4-dione or a salt thereof.

2. A pharmaceutical containing as an active ingredient the compound according to claim 1 or a salt thereof and a pharmaceutically acceptable liquid or solid additive.

3. The pharmaceutical according to claim 2, substantially not containing (−)-isomer.

4. The pharmaceutical according to claim 2, wherein 95 weight % or more of the total amount of the 5-(3,4-difluorophenyl)-5-[(3-methyl-2-oxopyridin-1(2H)-yl)methyl]imidazolidine-2,4-dione or a salt thereof in the pharmaceutical is (+)-isomer.

5. The pharmaceutical according to claim 4, wherein 98 weight % or more of the total amount of the 5-(3,4-difluorophenyl)-5-[(3-methyl-2-oxopyridin-1(2H)-yl)methyl]imidazolidine-2,4-dione or a salt thereof in the pharmaceutical is (+)-isomer.

6. The pharmaceutical according to claim 5, wherein 99.5 weight % or more of the total amount of the 5-(3,4-difluorophenyl)-5-[(3-methyl-2-oxopyridin-1(2H)-yl)methyl]imidazolidine-2,4-dione or a salt thereof in the pharmaceutical is (+)-isomer.

7. The pharmaceutical according to claim 2, wherein the pharmaceutical is an external preparation.

8. The pharmaceutical according to claim 7, wherein the external preparation is selected from the group consisting of a lotion, cream, liquid and ointment.

9. The pharmaceutical according to claim 7, containing pharmaceutically acceptable glycols.

10. The pharmaceutical according to claim 9, wherein the pharmaceutically acceptable glycols is propylene glycol or butylene glycol.

11. The pharmaceutical according to claim 7, containing water in the formulation.

12. The pharmaceutical according to claim 7, containing as an active ingredient 1 w/w % or more (+)-5-(3,4-difluorophenyl)-5-[(3-methyl-2-oxopyridin-1(2H)-yl)methyl]imidazolidine-2,4-dione or a salt thereof.

13. The pharmaceutical according to claim 12, containing as an active ingredient 3 w/w % or more (+)-5-(3,4-difluorophenyl)-5-[(3-methyl-2-oxopyridin-1(2H)-yl)methyl]imidazolidine-2,4-dione or a salt thereof.

14. The pharmaceutical according to claim 2, being transdermally administered.

15. The pharmaceutical according to claim 2, wherein the pharmaceutical is a treatment agent for a skin disease.

16. The pharmaceutical according to claim 15, wherein the skin disease is one or more selected from the group consisting of a localized scleroderma, atopic dermatitis, contact dermatitis, psoriasis, and acne.

17. A method of producing (+)-5-(3,4-difluorophenyl)-5-[(3-methyl-2-oxopyridin-1(2H)-yl)methyl]imidazolidine-2,4-dione, comprising optically resolving a racemate (±)-5-(3,4-difluorophenyl)-5-[(3-methyl-2-oxopyridin-1 (2H)-yl)methyl]imidazolidine-2,4-dione by chromatography using a column for optical separation.

18. (+)-5-(3,4-Difluorophenyl)-5-[(3-methyl-2-oxopyridin-1 (2H)-yl)methyl]imidazolidine-2,4-dione obtainable by optically resolving a racemate (±)-5-(3,4-difluorophenyl)-5-

[(3-methyl-2-oxopyridin-1(2H)-yl)methyl]imidazolidine-2,4-dione by chromatography using a column for optical separation.

19. A mixture of (+)- and (−)-isomers of 5-(3,4-difluorophenyl)-5-[(3-methyl-2-oxopyridin-1(2H)-yl)methyl]imidazolidine-2,4-dione, wherein the (+)-isomer exists at 90% ee or more to the (−)-isomer.

20. The mixture according to claim 19, wherein the (+)-isomer exists at 96% ee or more to the (−)-isomer.

21. The mixture according to claim 19, wherein the (+)-isomer exists at 99% ee or more to the (−)-isomer.

* * * * *

```
SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-methylanthranilic acid
<220> FEATURE:
<221> NAME/KEY: MISC_FEATURE
<222> LOCATION: (11)..(11)
<223> OTHER INFORMATION: dinitrophenyl

<400> SEQUENCE: 1

Xaa Leu Ala Gln Ala Val Arg Ser Ser Lys Xaa Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: dinitrophenyl
<220> FEATURE:
<221> NAME/KEY: MISC_FEATURE
<222> LOCATION: (3)..(3)
<223> OTHER INFORMATION: beta-cyclohexylalanyl
<220> FEATURE:
<221> NAME/KEY: MISC_FEATURE
<222> LOCATION: (5)..(5)
<223> OTHER INFORMATION: cysteine(Me)
<220> FEATURE:
<221> NAME/KEY: MISC_FEATURE
<222> LOCATION: (9)..(9)
<223> OTHER INFORMATION: N-methylanthranilic acid

<400> SEQUENCE: 2

Xaa Pro Xaa Gly Xaa His Ala Lys Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (1)..(1)
<223> OTHER INFORMATION: 7-methoxycoumarin-4-yl)acetyl
<220> FEATURE:
<221> NAME/KEY: MISC_FEATURE
<222> LOCATION: (6)..(6)
<223> OTHER INFORMATION: N-beta-(2,4-dinitrophenyl)-L-2,3-
      Diaminopropionyl

<400> SEQUENCE: 3

Xaa Pro Leu Gly Leu Xaa Ala Arg
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 7-methoxycoumarin-4-yl)acetyl
<220> FEATURE:
<221> NAME/KEY: MOD_RES
<222> LOCATION: (8)..(8)
<223> OTHER INFORMATION: Nva
<220> FEATURE:
<221> NAME/KEY: MISC_FEATURE
<222> LOCATION: (12)..(12)
<223> OTHER INFORMATION: dinitrophenyl

<400> SEQUENCE: 4

Xaa Arg Pro Lys Pro Val Glu Xaa Trp Arg Lys Xaa
1               5                   10
```